(12) United States Patent
Durell

(10) Patent No.: US 6,929,603 B2
(45) Date of Patent: Aug. 16, 2005

(54) VARIABLE VIEW ARTHROSCOPE

(75) Inventor: William E. Durell, North Barrington, IL (US)

(73) Assignee: Durell & Gitelis, Inc., North Barrington, IL (US)

( * ) Notice: Subject to any disclaimer, the term of this patent is extended or adjusted under 35 U.S.C. 154(b) by 0 days.

(21) Appl. No.: 10/795,792

(22) Filed: Mar. 8, 2004

(65) Prior Publication Data

US 2004/0236183 A1 Nov. 25, 2004

Related U.S. Application Data

(63) Continuation-in-part of application No. 10/694,446, filed on Oct. 27, 2003, which is a continuation-in-part of application No. 09/650,621, filed on Aug. 30, 2000, now Pat. No. 6,638,216.

(51) Int. Cl.[7] ................................................. A61B 1/00
(52) U.S. Cl. ........................ 600/173; 600/167; 600/168; 600/131
(58) Field of Search ................................. 600/130, 131, 600/133, 146, 147, 167, 168, 173; 359/823, 694, 699

(56) References Cited

U.S. PATENT DOCUMENTS

| | | |
|---|---|---|
| 1,726,268 A | 8/1929 | Jahr |
| 2,932,294 A | 4/1960 | Fourestier et al. |
| 2,987,960 A | 6/1961 | Sheldon |
| 3,357,433 A | 12/1967 | Fourestier et al. |
| 3,643,654 A | 2/1972 | Felbarg |
| 3,856,000 A | 12/1974 | Chikama |
| 3,880,148 A | 4/1975 | Kanehira et al. |
| 3,901,220 A | 8/1975 | Koyasu et al. |
| 3,918,438 A | 11/1975 | Hayamizu et al. |
| 4,140,364 A | 2/1979 | Yamashita et al. |

(Continued)

FOREIGN PATENT DOCUMENTS

| | | |
|---|---|---|
| WO | WO 95/25460 | 9/1995 |
| WO | WO 99/42028 | 8/1999 |
| WO | WO 01/39657 | 6/2001 |

Primary Examiner—John P. Leubecker
(74) Attorney, Agent, or Firm—Wilmer Cutler Pickering Hale and Dorr LLP

(57) ABSTRACT

A variable-view arthroscope or similar instrument (endoscope, etc.) includes a housing tube with an input end. The housing tube contains an input assembly and a portion of a light relay assembly. A control varies the position of the input assembly to change the viewing position of the arthroscope. In certain embodiments, the control uses external master magnets that rotate around an axis orthogonal to the longitudinal axis of the housing to drive internal slave magnets magnetically. This permits the housing to be sealed completely. In certain embodiments, a cam-axle assembly translates the rotational motion of the internal slave magnets to linear motion that drives a push rod that manipulates the input assembly.

15 Claims, 7 Drawing Sheets

U.S. PATENT DOCUMENTS

| | | | | |
|---|---|---|---|---|
| 4,191,468 A | | 3/1980 | Scully | |
| 4,640,577 A | | 2/1987 | Tsuno | |
| 4,697,577 A | | 10/1987 | Forkner | |
| 4,723,843 A | | 2/1988 | Zobel | |
| 4,838,247 A | | 6/1989 | Forkner | |
| 4,846,154 A | | 7/1989 | MacAnally et al. | |
| 4,858,002 A | | 8/1989 | Zobel | |
| 4,877,314 A | | 10/1989 | Kanamori | |
| 5,184,602 A | | 2/1993 | Anapliotis et al. | |
| 5,359,992 A | * | 11/1994 | Hori et al. | 126/4 |
| 5,424,877 A | | 6/1995 | Tsuyuki et al. | |
| 5,490,015 A | * | 2/1996 | Umeyama et al. | 359/824 |
| 5,603,687 A | | 2/1997 | Hori et al. | |
| 5,613,936 A | | 3/1997 | Czarnek et al. | |
| 5,643,176 A | | 7/1997 | Persidsky | |
| 5,743,846 A | | 4/1998 | Takahashi et al. | |
| 5,978,161 A | * | 11/1999 | Lemke | 359/824 |
| 6,099,467 A | * | 8/2000 | Kehr et al. | 600/167 |
| 6,110,105 A | | 8/2000 | Durell | |
| 6,139,490 A | | 10/2000 | Briedenthal et al. | |
| 6,364,830 B1 | | 4/2002 | Durell | |
| 6,371,909 B1 | | 4/2002 | Hoeg et al. | |
| 6,537,210 B1 | * | 3/2003 | Wulfsberg | 600/173 |
| 6,638,216 B1 | | 10/2003 | Durell | |
| 6,641,531 B2 | * | 11/2003 | Kehr | 600/172 |
| 2004/0236183 A1 | | 11/2004 | Durell | |

* cited by examiner

VARIABLE VIEW ARTHROSCOPE

RELATED APPLICATIONS

This application is a continuation-in-part of U.S. application Ser. No. 10/694,446, entitled Variable View Arthroscope with Charge Coupled Device filed Oct. 27, 2003, by inventor William E. Durell, which is a continuation-in-part of U.S. application Ser. No. 09/650,621, now issued as U.S. Pat. No. 6,638,216, entitled Variable View Arthroscope, filed Aug. 30, 2000 by inventor William E. Durell. The aforementioned applications are incorporated herein by reference.

FIELD OF THE INVENTION

The invention relates generally to arthroscopes, endoscopes and similar optical instruments and more specifically to variable view arthroscopes. The invention also relates to control mechanisms for medical devices.

BACKGROUND OF THE INVENTION

Arthroscopes and similar optical instruments, such as endoscopes, are used in medical applications, such as surgery and examination, as well as in non-medical applications that similarly involve visual inspection of a confined or inaccessible space that constitutes the working area. Although the present invention is described here with reference to an arthroscope or similar instrument employed for surgery, the invention may be useful for other applications and is intended to embrace all suitable variations.

Over the last fifteen or more years, minimally invasive surgery has become a mainstream surgical technique. Within the orthopedic field, in particular, arthroscopy and similar techniques that employ devices such as arthroscopes have become the most common surgical procedures. Minimally invasive surgery is less painful for the patient and, in most instances, can be performed more quickly and safely than surgery that requires greater invasion of the patient's body; other benefits of minimally invasive surgery include that administration of anesthesia is simpler for minimally invasive surgery, that patients heal more quickly, that hospital stays may be reduced in length or even eliminated, and that the procedures are more cost effective.

The value of using minimally invasive surgical techniques may be limited by the capabilities of the arthroscopes, endoscopes and other principal optical instruments employed. In particular, the rather limited field of view afforded by even the best available instruments that satisfy the dimensional and other requirement of surgical applications has limited the useful scope of minimally invasive surgical techniques. Typically, the larger the field of view, the greater the usefulness of the instrument for most applications.

Several methods for widening the field of view offered by arthroscopic/endoscopic instruments have been proposed, and some have been more successful than others, in view of challenges such as precision of construction, precision of relative movements, space requirements, optical distortions, and elimination of undesired ambient light. Various proposals involve different movable arrangements of optical elements provided in the input end of the instrument. Such an arthroscope incorporates a control mechanism that allows the operator to vary the view of the arthroscope by adjusting external controls that manipulate the movable arrangement of optical elements accordingly. Designing the control mechanism is challenging because the components that manipulate the movable arrangement of optical elements must provide sufficiently precise control and fit in the arthroscope.

An additional challenge in designing the control mechanism is to minimize, and preferably eliminate, the risk of leaks in the housing to seal moisture out of the system. Typically, reusable medical devices are sterilized by autoclaving. Autoclaving involves steam sterilization that normally reached 135 degrees Celsius. It is very difficult to seal steam out of the housing. If an endoscope control system is sealed with O rings or other sealing devices, in most cases, eventually enough moisture will leak into the housing to create condensation on the internal lenses during the cooling period following autoclaving. There is no convenient way to remove the condensation, so once the lenses are occluded, typically the arthroscope is no longer functional. Thus, it is desirable to seal the lenses in a leakproof housing. A housing through which moving parts, such as the components of common control mechanisms, penetrate cannot generally be guaranteed to be completely sealed so that it is leakproof, especially as parts like seals and gaskets wear down over time.

There is a need for a variable view arthroscope with a sealed housing. In particular, there is a need for a control mechanism for a variable view arthroscope that permits the housing to be completely sealed. In this specification and in the appended claims the term "arthroscope" means and should be interpreted to include an endoscope or any other similar optical instrument, whether used for surgery or other applications.

SUMMARY OF THE INVENTION

A variable view arthroscope in accordance with the present invention includes a housing and an input assembly. In various embodiments, the input assembly defines/determines the viewing position of the arthroscope. In certain embodiments, magnets link the external portion with the internal portion such that an external master magnet drives an internal slave magnet through the housing. In certain contemplated embodiments, external magnets rotate orthogonal to the longitudinal axis of the endoscope and drive internal magnets that are independently mounted on their own cam/axle assemblies. In certain embodiments, the magnetic control can be used to manipulate a push rod inside the housing that connects to the mounted elements of the input assembly and adjusts their position in synchronization with the motion of the external magnets. The external magnets may be controlled by control knobs that can be manipulate by an operator. In preferred embodiments, the control does not involve the use of moving parts that pass through the housing so that the housing can be sealed more effectively.

While a magnetic control mechanism is described herein in the context of a variable view arthroscope, it is contemplated that such a magnetic control mechanism may also be used for other types of devices, especially medical devices that have similar sealing requirements.

BRIEF DESCRIPTION OF THE DRAWINGS

For a fuller understanding of the present invention, reference should be made to the following detailed description taken in connection with the accompanying drawings, not drawn to scale, in which the same reference numerals indicate the same or similar parts, wherein.

DESCRIPTION OF THE PREFERRED EMBODIMENTS

Figure 1:
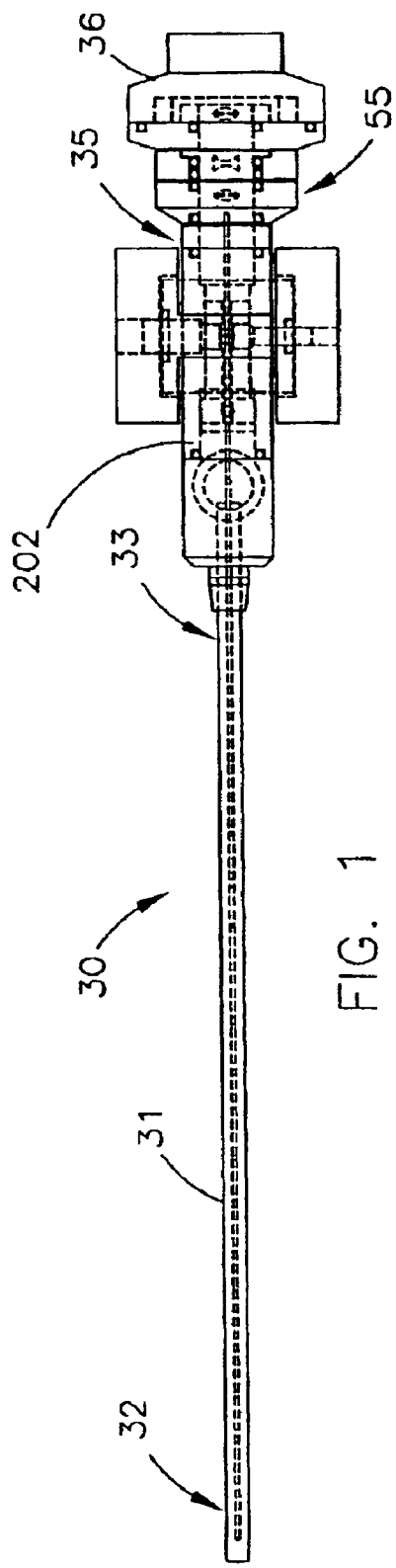
FIG. 1 is a plan view of a variable view arthroscope in accordance with an embodiment of the present invention.
Figure 2:
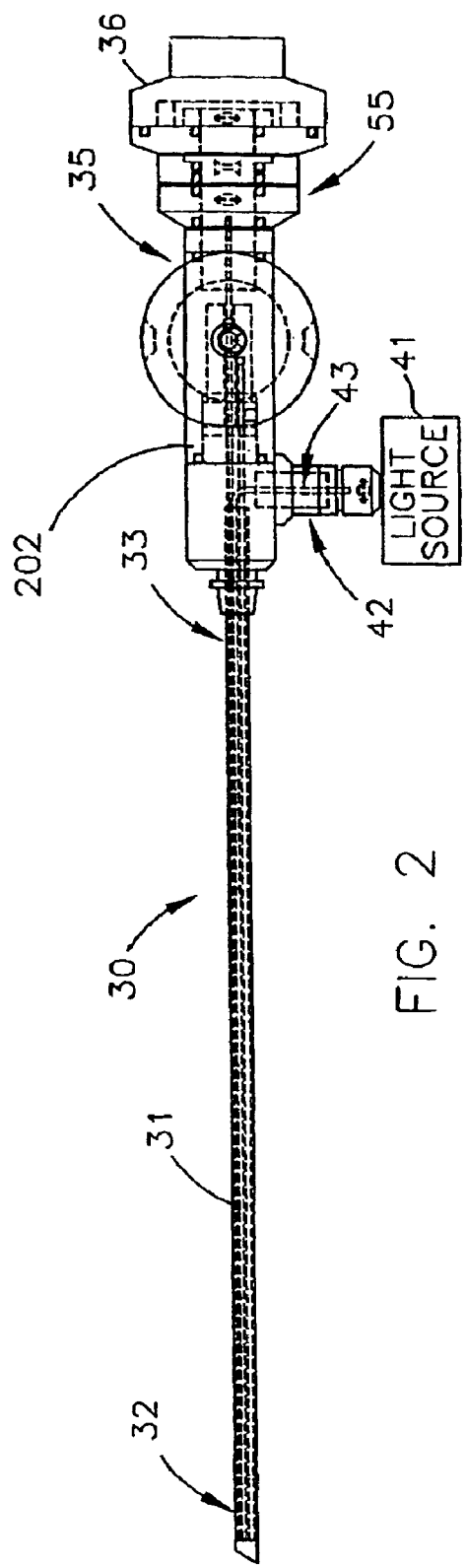
FIG. 2 is a side view of the variable view arthroscope of FIG. 1.

A variable view arthroscope in accordance with an embodiment of the present invention is shown in FIGS. 1 and 2. Although shown and described herein as an arthroscope providing up-down view variability, a similar configuration could be oriented so as to provide side-to-side view variability or view variability along any other axis. A variable view arthroscope, generally indicated at 30, includes an elongated housing tube 31, with an input end 32 and a control end 33, that extends along a central, longitudinal axis. Arthroscope 30 includes an outer control portion 35. Housing tube 31, and more specifically its control end 33, may extend into the outer control portion 35 of arthroscope 30. Generally, the object rays are captured at the input end 32 of housing tube 31, relayed to the control end 33, and recorded and displayed from the outer control portion 35 of arthroscope 30. As discussed herein, the object is formed of object rays and the object rays include an axial ray at the optical center of the object image, and rim rays at the outer edges or rims of the object image.

The control portion 35 ends with a CCD attachment 36. The CCD attachment 36 is connected by appropriate means to an image screen (not shown) to be viewed by a person using arthroscope 30. CCD attachment 36 may be of conventional construction and is not shown in detail. The outer control portion 35 may also include a control, such as a slide, for adjusting the view of the arthroscope 30, and a focusing lens assembly 55 for adjusting the focus of the arthroscope 30. The focusing lens assembly 55 may include a focusing lens, a zoom lens, and their controls. The focusing lens assembly directs the object received from the input end 32 into the CCD attachment 36. At the outer control portion 35, the arthroscope includes a portion of a lighting assembly 42, formed from a light source 41 that is connected to a light relay assembly 43. The lighting assembly 42 illuminates a viewing area beyond the input end 32 of the housing tube 31. The viewing area is preferably an area in front of the input end 32 of the arthroscope, from about 15 degrees below the longitudinal axis of the arthroscope tube 31 to about 105 degrees above the longitudinal axis of the arthroscope tube 31.

Referring now to FIGS. 3–6, the input end 32 includes an input assembly 50. In preferred embodiments, the input assembly 50 includes an input window 52, an input lens 54, a first mirror 56 and a prism 59. In obtaining an image of the object, the object rays pass from the viewing area into the input window 52 and through the input lens 54, and are reflected from the first mirror 56 to the prism 59.

The input end 32 of housing tube 31 is preferably beveled and closed by input window 52. The input window 52 is preferably a concentric spherical meniscus lens and formed so that the curvatures of the outer and inner surfaces are concentric to each other around a common centerpoint. Preferably, the centerpoint is on the centerline of the axle 90, which is on the front reflecting surface of the first mirror 56 (as discussed further below). Also, preferably, the centerpoint is on the optical axis of the input lens 54. If the centerpoint of the input window 52 is positioned on the input lens optical axis, a constant relationship is maintained between the refractive angles of the input object rays as the input lens 54 moves from position to position. As a result, the refraction of the object rays through the input window 52 is constant with respect to the input lens 54 and changing distortions which would be created by input window 52 are eliminated. The dimensions of the input window 52 preferably are selected to maximize the range of view of the arthroscope 30 in cooperation with the other elements of the object input assembly. Input window 52 may be formed of glass, sapphire or some other suitable material. The input window 52 is fixed in place, such as by adhesive, soldering, or by brazing, and also may be sealed to form a sealed closure for the end of the housing tube 31. Preferably, input end 32 of housing tube 31 is formed so that the edges of the housing tube 31 have a shape similar to the profile shape of the input window 52 and extend beyond the surface of input window 52 to afford the greatest protection to the input window 52 without interfering with the object rays during operation of the arthroscope 30.

The input lens 54 and the first mirror 56 are movable and together vary the view of the arthroscope 30 and direct the captured image to prism 59. The common axle around which both the input lens 54 and the first mirror 56 move and, with respect to which they are positioned, defines a preferred alignment of the input lens 54 and the first mirror 56. The input lens 54 of the object input assembly 50 is positioned inside the input end 32 of housing tube 31 proximate to the input window 52. In the embodiments illustrated in FIGS. 3 and 4, input lens 54 is a spherical or aspheric negative lens or lenses. However, any suitable lens may be used. The input lens 54 is movable and rotates around the axle 90. The input lens 54 rotates between a maximum upward view position and a maximum downward view position, approximately corresponding to and limited by the field of view afforded by the input window 52. The input lens 54 is preferably fixedly mounted on an input lens frame 80. The input lens frame 80 supports the input lens 54 at one end and pivots around the axle 90 at the other end. The input lens frame 80 is moved by a control mechanism. The input lens 54 is mounted on the input lens frame 80 so that the optical centerline or axis of the input lens 54 is directed to the centerline of the axle 90.

The first mirror 56 is accordingly positioned to reflect the object rays received from the input lens 54 to prism 59, which is fixed. The first mirror 56 pivots around the axle 90, in a motion complementary to that of the input lens 54. The centerline of the axle 90 is coplanar with the front reflecting surface of the first mirror 56. As the input lens 54 moves, the position of the first mirror must change to preserve the desired orientation of the object rays. Due to the geometry of mirrors, the angle change in a ray reflected from a mirror will be double the angle change in the reflecting plane of the mirror, such as when the mirror rotates from a first position to a second position. Consequently, the first mirror 56 rotates around the axle 90 at half the rate of angular change at which the input lens 54 rotates around the axle 90, in a complementary direction. That is, as the input lens rotates around the axle 90 through a first angle of rotation, the first mirror 56 pivots around the axle 90 through a second angle of rotation that is half the first angle of rotation. The first mirror 56 correspondingly rotates between a maximum upward view position and a maximum downward view position. Together with the movement of the input lens 54, the rotation of the first mirror 56 varies the view of the arthroscope 30. In alternative embodiments, the input lens 54 and the first mirror 56 may be moved between a series of pre-defined positions or may be moved to any position within the range of the arthroscope 30. The first mirror 56 is preferably mounted on a first mirror frame 86. A control adjusts the position of the first mirror 56. In the middle view of the input assembly 50, the reflecting surface of the first mirror 56 is horizontal with respect to the longitudinal orientation of tube 31 and the input lens 54 is positioned so the optical axis of lens 54 is at an angle 45 degrees up from the plane of mirror 56. In the illustrated embodiment, the center of the middle view is therefore 45 degrees up from the horizontal (FIG. 3), i.e., the longitudinal axis of the tube 31.

The object rays obtained through the input lens 54, first mirror 56, and prism 59 are preferably relayed to the outer control portion 35 of the arthroscope 30 via the relay lens assembly 60. It is preferred that the rays be relayed so as to preserve the quality of the image and to minimize aberrations. The prism 59 is fixed in position to reflect the captured object rays into the relay lens assembly 60. The prism 59 is preferably aligned to orient the reflected object rays parallel to the optical axis of the relay lens assembly 60, which axis is preferably parallel to the longitudinal axis of the housing tube 31. The relay lens assembly 60 optical centerline is preferably coaxial with the axial ray reflected from the prism 59. In various embodiments, the relay lens assembly 60 is a lens or a series of lenses, one alternative of which is commonly referred to as a field and relay lens system. In additional embodiments, the relay lens assembly 60 may be a graded index lens or other lens having a varying refractive index. In alternative embodiments, the relay lens assembly 60 may be replaced by an optical fiber coherent bundle. Although the relay lens assembly 60 is shown as being contained within the input end 32 of the housing tube 31, the relay lens assembly 60 typically extends further towards the control end 33. If the relay lens assembly 60 is replaced with a coherent bundle of optical fibers or is replaced with a graded index lens system, each will typically extend substantially along the length of housing tube 31. The relay lens assembly 60 may be of conventional construction, e.g., having an outer stainless steel sleeve for stability, or the relay lens assembly 60 may rest in a groove cut into relay light guide 120. The relay lens assembly 60 directs the object rays toward a receptor, such as a focusing lens assembly 55.

Figure 4:
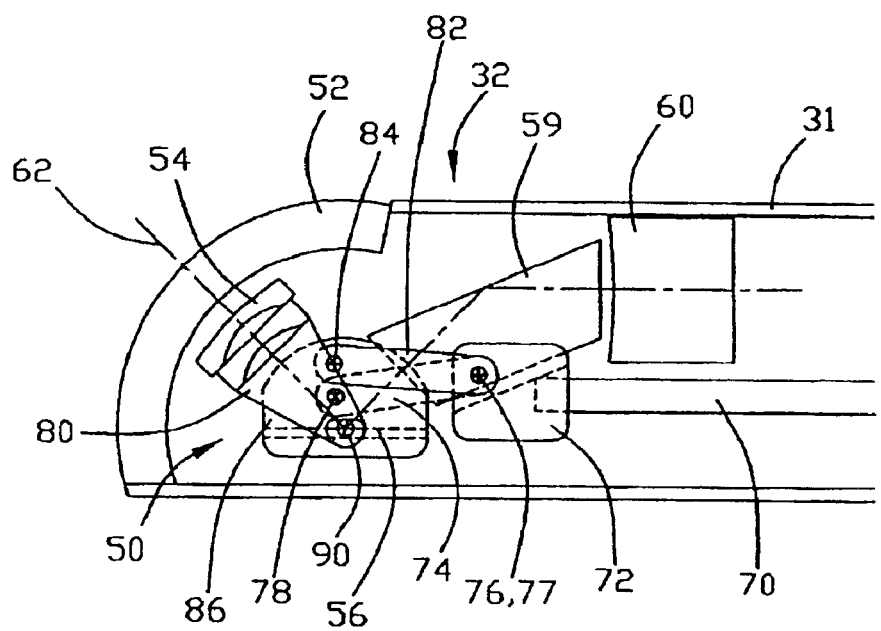
FIG. 4 is a sectional side view of the input assembly of the arthroscope of FIG. 1, showing the portions of an input assembly and related controls, in accordance with an embodiment of the present invention, adjusted for an intermediate view.
Figure 5:
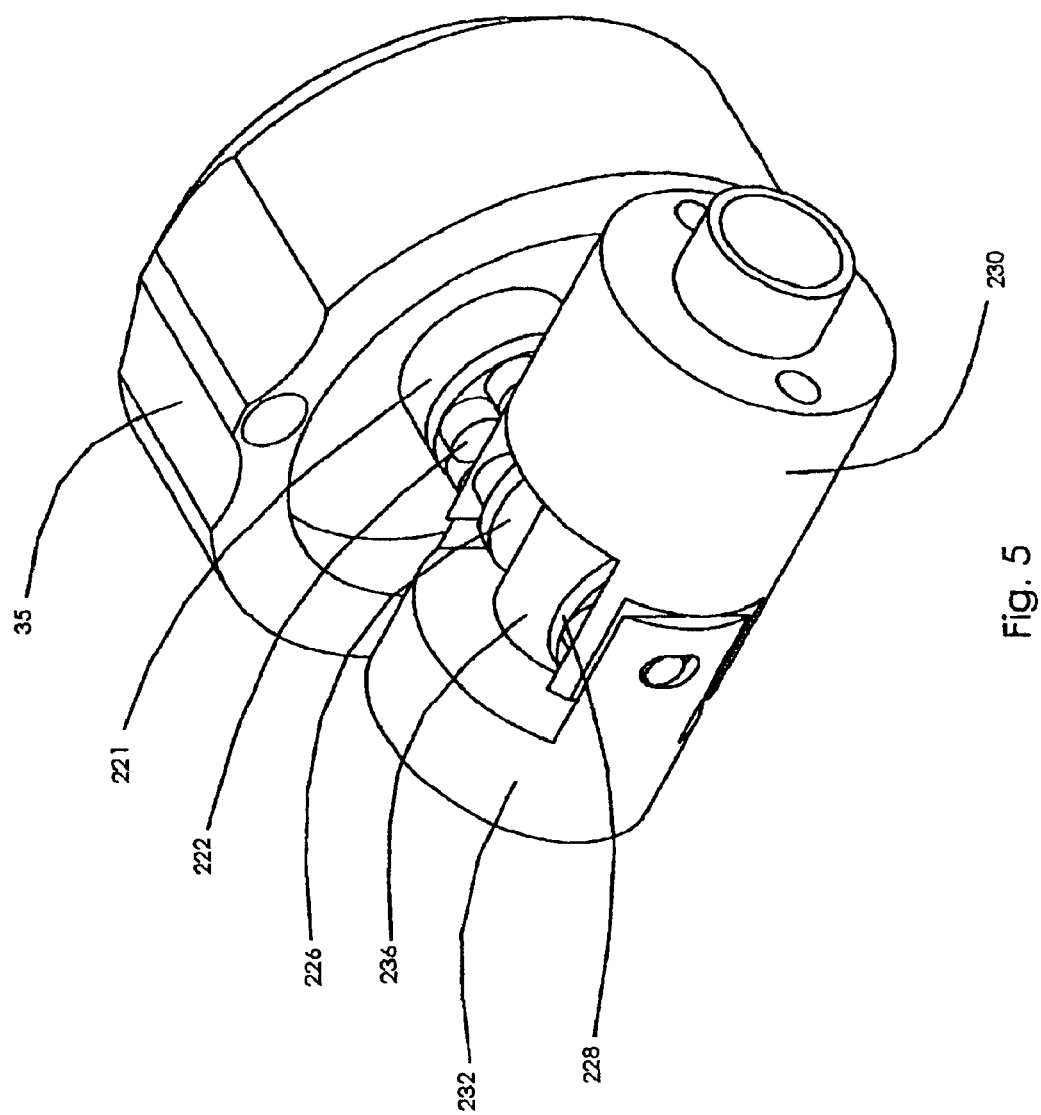
FIG. 5 is a perspective view of a portion of a control assembly for varying the view of a variable view arthroscope, constructed in accordance with an embodiment of the invention.
Figure 6:
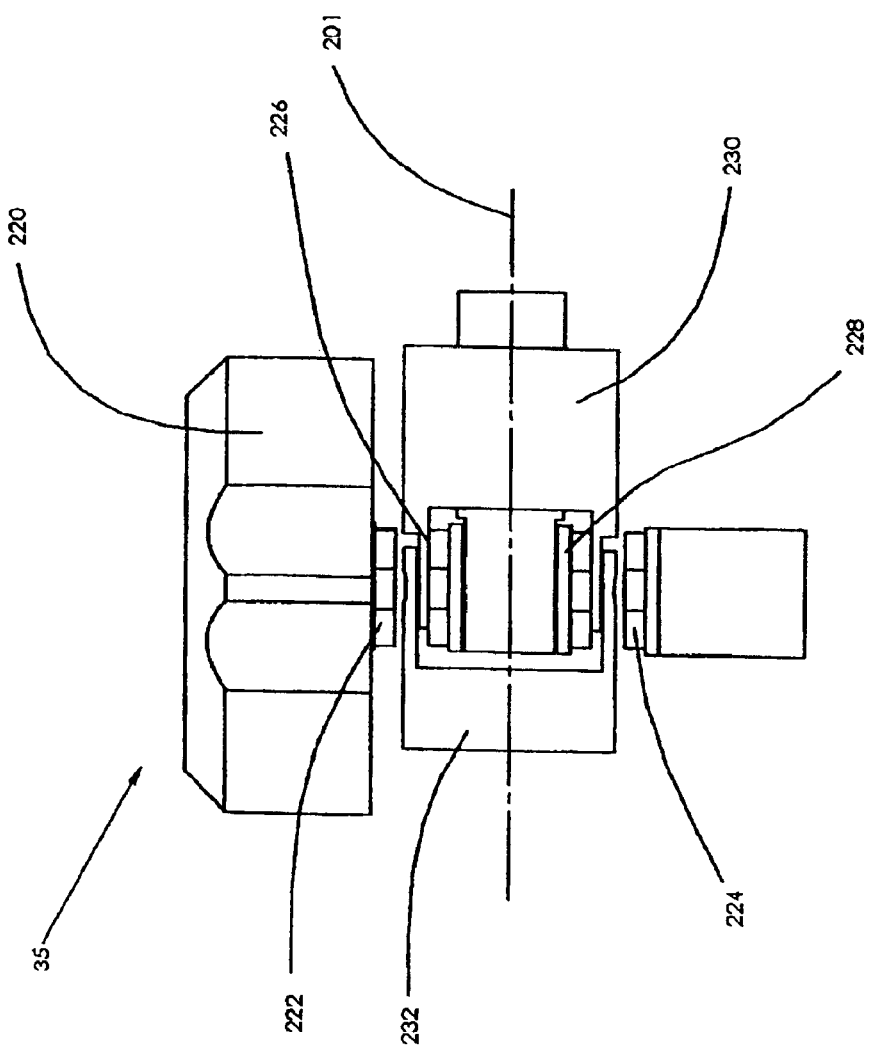
FIG. 6 is a plan view of a portion of the control assembly for varying the view of the variable view arthroscope, constructed in accordance with an embodiment of the invention.
Figure 7:
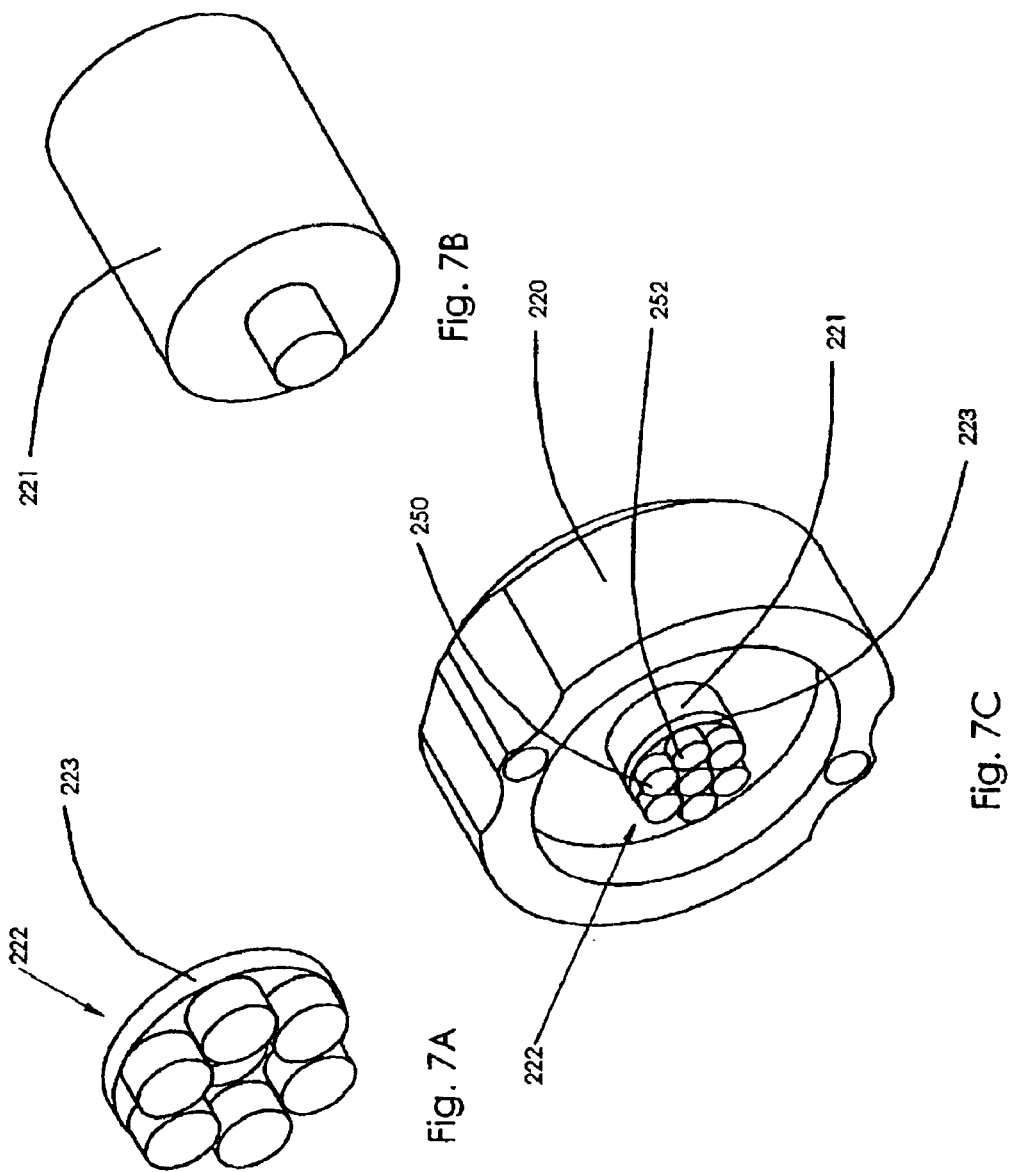
FIG. 7A is a perspective view of the external magnet assembly.
FIG. 7B is a perspective view of a shaft.
FIG. 7C is a perspective view of the assembled external magnet assembly, the control knob shaft, and the control knob.
Figure 8:
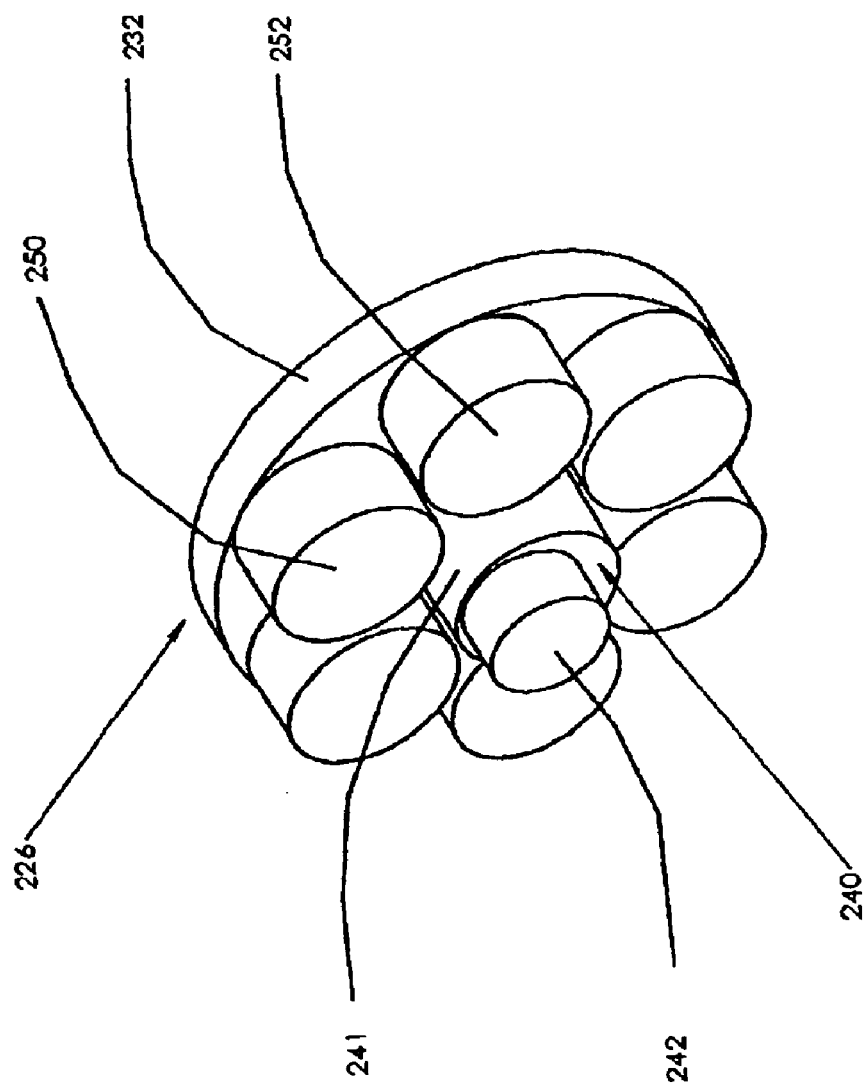
FIG. 8 is a perspective view of the assembled cam-axle and internal magnet assembly.

The movement of the input lens 54 and the first mirror 56 allows the viewing position of the arthroscope 30 and thus the particular input image captured in the arthroscope 30 to be variable. The control that adjusts the input lens 54 and the first mirror 56 adjusts them congruently to maintain the desired alignment. Referring to FIG. 4, preferably, a push rod 70 directs the motion of the input lens 54 and the first mirror 56. The position of the input lens 54 is adjusted by the push rod 70 engaging the input lens frame 80 through an input lens connecting rod 74. The input lens connecting rod 74 is connected to the push rod 70 at push rod yoke 72 by yoke pin 76. The input lens connecting rod 74 is connected to the input lens frame 80 through an input lens frame pin 78. As the push rod 70 moves back and forth along the longitudinal axis of the housing tube 31, the connecting rod 74 shifts the position of the input lens frame 80 and, hence, of the input lens 54. The position of the first mirror 56 is adjusted by the push rod 70 engaging the first mirror frame 86 through a first mirror connecting rod 82. The first mirror connecting rod 82 is connected to the push rod 70 at push rod yoke 72 by yoke pin 77. Yoke pins 76 and 77 are disposed on opposite sides of the push rod yoke 72 and are coaxial. The first mirror connecting rod 82 is connected to the first mirror frame 86 through a first mirror frame pin 84. As the push rod 70 moves back and forth, the first mirror connecting rod 82 adjusts the angle of the first mirror 56.

The first mirror connecting rod 82 is fastened to the push rod yoke 72 at yoke pin 77 and the input lens connecting rod 74 is connected to the yoke at yoke pin 76. Because yoke pins 77 and 76 are coaxial, both connecting rods move synchronously. Preferably, the distance from the axle 90 to the input lens frame pin 78 is one half the distance from the axle 90 to the first mirror frame pin 84. As the push rod 70 moves laterally a certain distance, the angular change of the input lens 54 is preferably twice the angular change of the first mirror 56 since the radius of the input lens arc is one half the radius of the first mirror arc. The illustrated positioning and relative proportions of the connecting rods, axle and input lens frame pin and first mirror frame pin in FIG. 4 preferably minimize any error in the relative angular changes. It should be understood that any mechanical arrangement that preserves the desired geometries of the mirrors and the input lens is suitable; for example, more than one push rod may be effective.

To minimize distortion in the recorded image, preferably, the object ray path lengths remain constant as the view of the arthroscope varies. The object axial ray 62 passes through the optical center of the input lens 54 to the center of the first mirror 56. This distance is fixed because the center of the first mirror 56 is fixed on the centerline of the axle 90 around which the input lens 54 rotates with a constant radius. The object axial ray 62 then reflects from the center of the first mirror 56 to prism 59, which is fixed with respect to the first mirror 56. The axial ray then reflects from the prism 59 along the optical axis of the relay lens assembly 60, which is fixed with respect to prism 59. Because each segment of the object axial ray 62 has a fixed length, the length of the object axial ray 62 from the input lens 54 to the relay lens system 60 remains constant as the view of the arthroscope 30 varies. The object rim rays 64 pass through the input lens 54 to the first mirror 56. Because axial ray 62 is coaxial with the optical axis of input lens 52, all object rim rays 64 are symmetric about axial ray 62. As long as all object rays are reflected or refracted symmetrically to any plane normal to axial ray 62, such as the first lens of the relay lens system 60, the length of the object rays remain constant. In some embodiments of the present invention, this feature may allow the view to change without changes in distortion and image quality.

Figure 3:
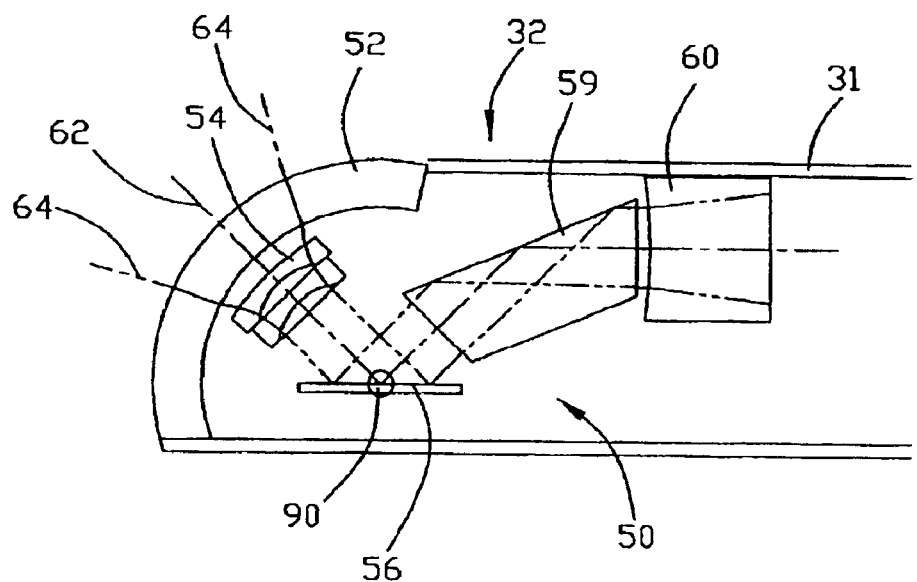
FIG. 3 is a sectional side view of the input assembly of the arthroscope of FIG. 1, showing the axial ray and rim rays through the input assembly, in accordance with another embodiment of the present invention, adjusted for an intermediate view.

An alternative embodiment, rather than prism 59, a second mirror may orient the image rays reflected from the first mirror 56 into the relay lens assembly 60. The second mirror receives object rays and internally reflects them in the desired direction. Also, as illustrated in FIGS. 3 and 4, the input lens 54 may be a doublet consisting of two spherical lenses, or aspheric lenses, or a combination of spherical and aspheric lenses.

The lighting assembly 42, illustrated in FIG. 2, includes a light source 41 with an external optical fiber light guide to transmit light to the light relay assembly 43 that extends into the arthroscope 30. Any conventional external light source and light guide may be used. Typically, the external light source 41 is connected at an angle oblique to the axis of the housing tube 31. The lighting assembly 42 may include a condenser lens to focus light from the external source 41 onto the input end of the light relay assembly 43. The light relay assembly 43 reorients the light along the longitudinal axis of the housing tube 31 and transmits the light to the end 32 of the housing tube 31. The light relay assembly 43 may include one or more optical fiber bundles. In some embodiments, the light relay assembly 43 is an optical fiber bundle that extends to the input end 32 of the arthroscope 30. In alternative embodiments, the light relay assembly 43 may include structures other than optical fiber bundles.

Control assembly 35 includes a first external magnet assembly 222 and a second external magnet assembly 224. Because the mechanical arrangement and operation of external magnet assemblies 222 and 224, and their respective internal magnets (discussed below) are identical, and assembly 35 is symmetrical about a plane extending vertically through line 201, control assembly 35 is described primarily with reference to external magnet assembly 222 and associated components.

External magnet assembly 222 is composed of a plurality of disc magnets set in a circle around the axis of magnetic backing plate 223. The preferred embodiment is six disc magnets set with alternating north and south poles facing outward. The magnets are affixed to magnet backing plate 223 with adhesive, solder, or brazing. Magnet 250 is placed with its north face facing outward. The next magnet, magnet 252, is set with its south face facing outward. This alternating pattern of north and south faces facing outward is repeated around the circle of magnets. Magnet backing plate 223 is made of iron, steel, or other material that can be magnetized. The advantage to this is that the magnetized backing plate 223 will reflect the magnetic flux outward thus increasing the magnetic efficiency of the magnet assembly. All of the magnetic assemblies, both internal and external, are constructed in this manor.

External magnetic assembly 222 is glued, soldered, brazed, or other method of affixing it to control knob shaft 221. The centerline of external magnet assembly 222 and control knob shaft 221 are coaxial. Control Knob shaft 221 is attached to control knob 220 either by a press fit into a hole in the center of control knob 220 or by gluing, soldering, or brazing it in place. The centerline of control knob shaft 221 and control knob 220 are coaxial.

The internal magnet assembly is similar to the external magnet assembly. Internal magnet assembly 226 is affixed to the cam-axle 240 in the same manor as the external magnets assembly is affixed to the control knob shaft.

Alternatively, the magnet assemblies may each be replaced by a single magnet, e.g., a 4 pole, 1 face magnet.

In alternative embodiments, the slide 232 may also be electrically driven. Slide 148 may be driven by a step motor. A step motor may drive cam/axle 162, or cam/axle 162 may be replaced with, for example, a jack screw engaging slide 232. The step motor and jack screw are preferably internal to the arthroscope 30 and mounted parallel to the motion of slide 232. Slide 232 may also be driven with a piezoelectric positioner mounted internally to the arthroscope 30. The arthroscope 30 may be electrically operable by electrical buttons or by operating software on a computer, for example.

Operation of the arthroscope 30 can now be considered. At the outset, light from external source 41 is focused upon the end of the light relay assembly 43. Light passes through the light relay assembly 43 and illuminates a surgical working area just beyond the input end 32 of the arthroscope 30. Light reflected from the working area passes through input window 50 and input lens 54 as object rays which impinge on first mirror 56. The object rays are directed from the first mirror 56 to impinge upon the second mirror 58 or prism 59. From the second mirror 58 or prism 59 the object rays are re-directed toward the input end of the relay lens assembly 60. The relay lens assembly 60 supplies the image to the CCD attachment 36, through focusing lens assembly 55, to be viewed by the surgeon or other person using the arthroscope 30.

If the person using arthroscope 30 is dissatisfied with the image available through the CCD attachment 36, control knobs 149, 150 may be used to provide an image of a different portion of the surgical region. In this way the image supplied to the surgeon or other person using the instrument 30 can be and is varied to a substantial extent with no change in the position of the instrument. In effect, the overall viewing range of the instrument 30 may extend from about 15 degrees below the longitudinal axis of the housing tube to about 105 degrees above the axis of the housing tube, with no need to change the axis of the instrument. Further alteration or correction of the image may be effected by appropriate software.

In alternate embodiments, push rod 70 may be driven by a magnetically coupled control. FIGS. 5 through 9 illustrate a control assembly 35 for operating the variable view feature of arthroscope 30. The housing 202 (FIG. 1) encloses the internal mechanism of the magnetic control system and supports the control knobs and the external mechanism of the magnet control system. Control assembly 35 FIGS. 5 and 6 uses internal magnet assemblies and external magnet assemblies to couple the external control manipulated by an operator to the internal control that adjusts push rod 70 (FIG. 4) accordingly. A control knob 220 will typically be manipulated by a human operator to change the view of arthroscope 30 in the manner described above. A corresponding second control knob that is disposed opposite to control knob 220 is not shown in FIGS. 5 and 6 for convenience. Control assembly 35 includes a first external magnet assembly 222, and a second external magnet assembly 224. Because the mechanical arrangement and operation of external magnet assemblies 222 and 224, and their respective internal magnet assemblies (discussed below) are virtually identical, and control assembly 35 is symmetric about a vertical plane extending through line 201, control assembly 35 is described primarily with reference to external magnet assembly 222 and associated components.

Control knob 220 is connected to a shaft 221 that passes through the center of external magnet assembly 222 and to which external magnet assembly 222 is affixed. External magnets 222 and 224 act as master magnets that drive internal slave magnets to induce reciprocal motion inside the housing of arthroscope 30. Rotation of control knob 220 causes shaft 221 to rotate, which in turn causes external magnet 222 to rotate. External magnets 222 and 224 rotate around the axis of the respective shafts on which they are disposed, an axis that is orthogonal to the longitudinal axis of arthroscope 30 (defined primarily by the longitudinal axis of housing tube 31), indicated by line 201.

Briefly, the internal portion of control assembly 35 has two primary components, an internal magnet holder 230 that supports two internal magnet assemblies, and a slide 232, that is engaged when motion is induced in the internal magnets. Internal magnet holder 230 supports the first internal magnet assembly 226 and the second internal magnet assembly 228. First internal magnet assembly 226 operates reciprocally with first external magnet assembly 222, while second internal magnet assembly 228 operates reciprocally with second external magnet assembly 224. Internal magnet assemblies 226 and 228 are mechanically coupled to slide 232 so that circular motion of the magnets translates to linear motion of slide 232. Push rod 70 is rigidly connected to slide 232. Linear motion of slide 232 along the longitudinal axis of arthroscope 30 moves push rod 70 to vary the view.

Figures 9A, 9B:
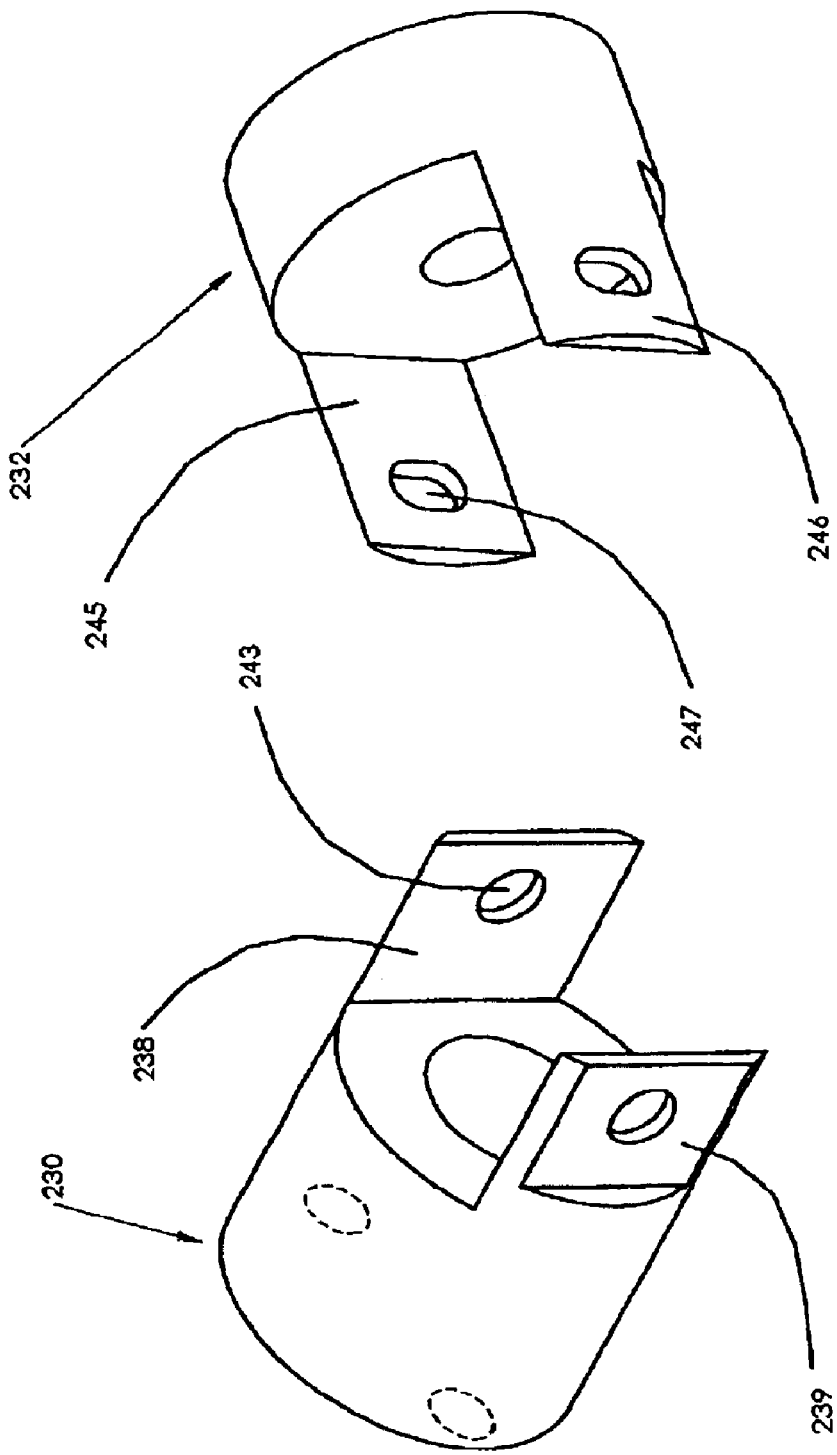
FIG. 9A is a perspective view of an internal magnet holder used in the control assembly of FIG. 5.
FIG. 9B is a perspective view of a slide used in the control assembly of FIG. 5.

Referring now also to FIG. 9A, internal magnet holder 230 is formed of a substantially cylindrical body with two flanges 238 and 239 that are used to support internal magnets 226 and 228, respectively. Each internal magnet assembly 226 and 228 is mounted between the flanges 238 and 239 on its own separate cam-axle assembly, shown in FIG. 8. Internal magnet assembly 226 is affixed to an axle 241 of a cam-axle assembly 240. Axle 241 passes through and is supported by an aperture 243 in flange 238 which extends from internal magnet holder 230. Axle 241 is held in an aperture in flange 238 by the magnetic attraction between internal magnet assembly 226 and external magnet assembly 222. Axle 241 is allowed to rotate in internal magnet holder aperture 243. The outer portion of cam-axle assembly 240 includes a cam 242 that is used to mechanically connect to slide 232. Internal magnet assembly 228 is affixed to cam-axle assembly 240. Internal magnet holder 230 also includes lens retainer 236 that is used to hold internal magnet assemblies 226 and 228 in place. Lens retainer 236 prevents internal magnet assemblies 226 and 228 from becoming dislodged in case of an extreme jolt to the arthroscope and are also useful during assembly to hold internal magnets 226 and 228 in place before external magnet assemblies 222 and 224 positioned. In an alternative embodiment, a 4-pole, 1 face magnet may be used in place of each of the external and/or internal magnet assemblies.

Referring now also to FIG. 9B, like internal magnet holder 230, slide 232 is also formed of a substantially cylindrical body and includes two flanges 245 and 246. Flanges 238 and 239 fit in between flanges 245 and 246 when internal magnet holder 230 and slide 232 are coupled. Cam 242 of cam-axle assembly 240 is inserted in an elongated hole shaped aperture 247 of flange 245 in slide 232. When cam-axle assembly 240 rotates driven by control knob 220, cam 242 of cam-axle assembly 240 engages flange 245 in slide 232. As cam 242 rotates in response to rotation of external magnet assembly 222, and thus rotation of internal magnet assembly 226, slide 232 is driven linearly fore and aft parallel to the longitudinal axis of arthroscope 30.

In certain embodiments, magnet assemblies 224, 226, 228 and 230 are all identical. The magnets are annular and relatively flat. In each external magnet assembly pairing, the north poles of the external magnet assemblies are directly opposite the south poles of the corresponding internal magnet assemblies. Thus the north poles of external magnet assembly 222 are opposite the south poles of internal magnet assembly 226 and the north poles of external magnet assembly 224 are opposite the south poles of internal magnet assembly 228. The control knobs are mounted on opposite sides of arthroscope 30 but are connected to each other. Rotation of control knob 220 also rotates the other control knob. Each internal magnet assembly is attracted to its corresponding internal magnet assembly. Thus, when the external magnet assembly is rotated, the internal magnet assembly follows.

One advantage of control assembly 200 is that the housing can be completely sealed to prevent internal condensation. Because the coupling between the external controls and the internal controls is magnetic, and not mechanical, no moving parts need to extend through the housing. Another advantage of control assembly 200 is that the magnets have a large mechanical advantage over the motion of the slide and push rod. For example, in one exemplary embodiment, a point on the outside circumference of a control knob moves through 1.2 inches from full down to full up, while the push rod moves 0.02 inches, a mechanical advantage of 60 to 1. The same system can be used in some embodiments to drive both the push rod and additional focusing or zoom lenses.

Not shown in the drawings are control knob spacers which fit into the top and bottom holes shown near the rim of the control knobs. With the spacers in place, the control knobs are properly spaced and held rigidly together. 'O' rings fit in the fillet formed by the control knob shaft the control knob, engage a cavity in the body housing and keep the control knobs centered. The 'O' rings also offer resistance to the rotation of the control knobs and thus provide "feel."

Several parts of instrument 30 can be modified from those illustrated without appreciable effect on overall operation of instrument 30. For example, the input assembly may be modified to use a different optical arrangement, to use a CCD, or in other ways. For example, the push rod 70 may be modified; the push rod 70 constitutes an optional mechanism for operating the input lens and first mirror but any mechanism that will move the input lens and first mirror in the relationship described can be used. The cam/axle and slide control mechanism may also be altered. The angle of the bevel of the outer end of housing tube 31 may be varied as desired; a curved shaped similar to the profile shape of the input window and extending beyond the input window so as to provide maximum protection to the input window without interfering with the object rays is preferred, but may depend on the primary use for instrument 30. It will be recognized that use of a CCD unit for a display is not essential. The software used for the display may vary appreciably.

The language used herein is used for purposes of reference and not limitation. While the invention has been particularly shown and described with reference to preferred embodiments, it will be apparent to those skilled in the art that various modifications and alterations can be made in the device of the present invention without departing from the spirit and scope of the invention.

What is claimed is:

1. A variable view arthroscope having more than one viewing position in a range between a first viewing position and a second viewing position, comprising:
    a housing having an input end and a control end, the housing having a longitudinal axis;
    an input assembly disposed in the input end of the housing, a position of the input assembly defining a viewing position of the arthroscope, the position being adjustable;

a push rod mechanically connected to the input assembly to adjust the position of the input assembly;

a first magnet assembly disposed outside the housing, the first magnet assembly being rotatable around a first internal axis orthogonal to the longitudinal axis; and a second magnet assembly disposed inside the housing, the second magnet assembly being rotatable around a second internal axis orthogonal to the longitudinal axis, said second magnet being mechanically coupled to the push rod, wherein rotation of the first magnet assembly magnetically induces rotation of the second magnet assembly, and wherein rotation of the second magnet assembly creates a linear motion of the push rod along the axis.

2. The arthroscope of claim 1 wherein at least one of the first magnet assembly and the second magnet assembly is an array of circularly disposed disc magnets.

3. The arthroscope of claim 2 wherein each of said magnet assemblies is a said array.

4. The arthroscope of claim 1 wherein at least one of the first magnet assembly and the second magnet assembly is a 4-pole, 1 face magnet.

5. The arthroscope of claim 4 wherein each of said magnet assemblies is a said magnet.

6. The arthroscope of claim 1, wherein the housing is sealed so that no moving parts penetrate the housing.

7. The arthroscope of claim 1, further comprising a control knob disposed outside the housing for rotating the first magnet assembly.

8. The arthroscope of claim 1, further comprising an internal magnet holder for supporting the second magnet assembly and a slide for driving the push rod, the internal magnet holder and the slide being coupled by a cam-axle assembly, the second magnet assembly being disposed on the axle of the cam-axle assembly and the cam engaging the slide.

9. An arthroscope control for manipulating an input assembly of a variable view arthroscope, the arthroscope having a housing extending along a longitudinal axis, the arthroscope having more than one viewing position, including a first viewing position and a second viewing position, the input assembly being movable and the orientation of the input assembly determining the viewing position of the arthroscope, comprising:

a push rod having an input assembly end and a slide end disposed inside the housing, the push rod being connected to the input assembly at the input assembly end, the push rod being laterally movable between a first position corresponding to the first viewing position and a second position corresponding to the second viewing position;

a control knob to select a position for the object input assembly disposed outside the housing, the control knob being rotatable;

a first magnet assembly mounted on the control knob, the first magnet assembly being annular and fixedly mounted on a shaft of the control knob, the first magnet assembly being rotatable with the control knob;

a second magnet assembly disposed inside the housing, the second magnet assembly being rotatable, the second magnet assembly being magnetically coupled to the first magnet assembly;

a cam-axle assembly to translate the rotational motion of the second magnet assembly into lateral motion, the cam-axle assembly being connected to the second magnet assembly and coupled to the push rod at the slide end, the cam-axle assembly inducing lateral motion in the push rod to move the push rod between the first position and the second position in response to rotation of the control knob.

10. The arthroscope control of claim 9, wherein the housing is sealed so that no moving parts penetrate the housing.

11. The arthroscope control of claim 9, wherein the first magnet and the second magnet are 4-pole, 1 face magnets.

12. The arthroscope of claim 9 wherein at least one of the first magnet assembly and the second magnet assembly is an array of circularly disposed disc magnets.

13. The arthroscope of claim 12 wherein each of said magnet assemblies is a said array.

14. The arthroscope of claim 9 wherein at least one of the first magnet assembly and the second magnet assembly is a 4-pole, 1 face magnet.

15. The arthroscope of claim 14 wherein each of said magnet assemblies is a said magnet.

* * * * *